(12) United States Patent
Baker et al.

(10) Patent No.: US 7,178,522 B2
(45) Date of Patent: Feb. 20, 2007

(54) AGENTS AND N2O DETECTION APPARATUS

(75) Inventors: Jeff Baker, Pewakee, WI (US); Eugene Palatnik, Pewaukee, WI (US); Rahul A. Patil, Waukesha, WI (US)

(73) Assignee: Smiths Medical PM, Inc., Waukesha, WI (US)

( * ) Notice: Subject to any disclaimer, the term of this patent is extended or adjusted under 35 U.S.C. 154(b) by 0 days.

(21) Appl. No.: 10/856,814

(22) Filed: Jun. 1, 2004

(65) Prior Publication Data

US 2005/0263154 A1 Dec. 1, 2005

(51) Int. Cl.
*A61M 16/00* (2006.01)
*A62B 7/00* (2006.01)
*F16K 31/02* (2006.01)

(52) U.S. Cl. .......................... 128/204.22; 128/205.12; 128/205.27; 128/205.28

(58) Field of Classification Search ........... 128/201.25, 128/203.12, 203.13, 204.16, 204.18, 204.21, 128/204.22, 204.24, 205.12, 205.27, 205.29, 128/910, 914
See application file for complete search history.

(56) References Cited

U.S. PATENT DOCUMENTS

| | | | |
|---|---|---|---|
| 3,867,936 A | 2/1975 | Kelley | |
| 3,941,573 A * | 3/1976 | Chapel | 96/135 |
| 4,108,172 A * | 8/1978 | Moore, Jr. | 128/205.12 |
| 4,228,125 A * | 10/1980 | Lobdell et al. | 422/46 |
| 4,266,539 A * | 5/1981 | Parker et al. | 128/204.26 |
| 4,442,856 A | 4/1984 | Betz | |
| 5,038,792 A * | 8/1991 | Mault | 600/531 |
| 5,044,363 A | 9/1991 | Burkhart | |
| 5,057,822 A | 10/1991 | Hoffman | |
| 5,109,838 A * | 5/1992 | Elam | 128/203.12 |
| 5,231,980 A | 8/1993 | Filipovic et al. | |
| 5,515,715 A | 5/1996 | Sowinski | |
| 5,576,493 A | 11/1996 | Sowinski | |
| 5,590,644 A * | 1/1997 | Rosenkoetter | 128/201.13 |
| 5,592,933 A * | 1/1997 | Zucchi | 128/201.13 |
| 5,634,426 A * | 6/1997 | Tomlinson et al. | 116/207 |
| 5,673,688 A | 10/1997 | Tham et al. | |
| 5,826,575 A * | 10/1998 | Lall | 128/205.12 |
| 5,850,833 A * | 12/1998 | Kotliar | 128/202.12 |
| 6,561,185 B1* | 5/2003 | Kroll | 128/202.12 |
| 6,623,544 B1* | 9/2003 | Kaura | 95/3 |
| 6,745,771 B2* | 6/2004 | Castor et al. | 128/205.27 |
| D527,106 S * | 8/2006 | Baker et al. | D24/164 |
| D527,107 S * | 8/2006 | Baker et al. | D24/164 |
| 2003/0205673 A1 | 11/2003 | Williams | |

* cited by examiner

*Primary Examiner*—Henry Bennett
*Assistant Examiner*—Nihir Patel
(74) *Attorney, Agent, or Firm*—Louis Woo (57) ABSTRACT

A detector that monitors the presence of halogenated agents and the presence of N2O includes a base to which a filter cannister is removably coupled. The cannister has an input for accepting exhalent from a patient or an anesthesia machine and an outlet for outputting the filtered exhalent as gases to the base. The filtered gases are routed a gas measurement or monitor cell housed in the base. The cell has a halogenated agents sensing system and a N2O sensing system. When the filter material in the filter cannister could no longer filter out the halogenated agents, the agents are passed from the filter to the measuring cell, which would detect the presence of the halogenated agents. An audible alarm sounds when halogenated agents are detected. This tells the user that it is time to replace the filter cannister.

18 Claims, 9 Drawing Sheets

Power Supplies

Simplified flow chart of agent control processor (PIC)

FIG. 13

Main Processor Information Flow (following system initialization)

AGENTS AND N2O DETECTION APPARATUS

FIELD OF THE INVENTION

The present invention relates to detection of halogenated agents and gases used in an anaesthetic setting and more particularly to an apparatus for detecting the presence of halogenated agents and N2O (nitrous oxide).

BACKGROUND OF THE INVENTION

When anaesthetic gases are used in a hospital environment, such as for example in an emergency or operating room, the halogenated agents from the gases or the exhalent of the patient have to be purged from the immediate enclosed environment to protect the people in that enclosed environment. To achieve this purging of the halogenated agents, the patient, and the anesthetic machine to which the patient most likely is attached, are connected to a scavenging system whereby the halogenated gases are exhausted to the outside environment away from the enclosed operating room. Oftentimes, N2O is also used in an operating room.

To remove the anesthetic gases from the exhalent of a patient, there has been disclosed in the prior art the use of an adsorbent unit in the form of disposable cartridges (U.S. Pat. No. 3,941,573, U.S. Pat. No. 3,867,936 and U.S. Pat. No. 5,044,363) in which the patient's exhalent is adsorbed. These disposable cartridges contain adsorbent fillers that react with and absorb the halogenated gases. As the amount of anesthetic gases is absorbed, the material in the disposable cartridges or containers saturates and the cartridges would increase in weight and as a consequence will no longer adsorb the anesthetic gases after a given time. Thus, after a certain amount of time or after the cartridges reach a certain weight, these cartridges are replaced with new cartridges.

There has also been disclosed in the prior art (U.S. Pat. No. 5,231,980) a process for recovering the halogenated hydrocarbons from a patient's exhalent. To accomplish this, the '980 patent discloses the use of a sensor at the exhaust line to sense the presence of anesthetics exiting from the cannister that adsorbs the halogenated hydrocarbons. The sensor may be connected by a signal line to the anesthesia machine to provide an indication to the anesthetist that the adsorbent cannister should be replaced so that the recovery of the anesthetics could continue. For the device disclosed in the '980 patent, the cannister has to be connected to the anaesthesia machine by both a gas line and a signal line. Insofar as the cannister has to be connected to the anesthesia machine, it is considered as part of the anesthesia machine and accordingly is cumbersome and not meant for portability.

A need therefore exists for a portable standalone system that has a replaceable cannister adaptable for adsorbing halogenated agents. The portable standalone system could be used in any environment, including an enclosed room in which halogenated hydrocarbons may be released from the exhalent of a patient.

The present invention detection device is used where it is not possible to vent the anesthetic gases directly into an operating room, since doing so would cause the air in the operating room to exceed OSHA limits in a relatively short period of time, as for example 10 minutes in the instance where the operating room is a small room in a field hospital, or a veterinary operating room where a veterinarian is treating an animal.

SUMMARY OF THE INVENTION

The halogenated agents and N2O detection device of the instant invention is a portable device that has a base housing to which a replaceable filter device in the form of a cannister is secured. The cannister contains materials that adsorb the halogenated agents from the exhalent of the patient that may be mixed with the anesthetic gases from an anesthesia machine. The patient's exhalent is input to the cannister, which is secured to a base housing in such a way that the outlet of the cannister is fitted to an input port at the base. The patient's exhalent, after passing through the cannister and sucked through the input port of the base, is further filtered by a contaminant filter. Thereafter, the filtered gases are routed to a measuring cell that contains a metal oxide semiconductor sensor and an optional optical sensor. Halogenated agents that are not adsorbed by the agents adsorbent material in the cannister are detected by the metal oxide semiconductor sensor, while N2O, which is not adsorbed by the material in the cannister, is detected by the optical sensor.

If halogenated agents are detected, an alarm, in the form of an audible tone, is output from the base housing to alert the user that the material inside the cannister is no longer adsorbing the halogenated agents. An indicator, in the form of a light, on the display panel of the base, is also lit to inform the user that the cannister needs to be replaced. If N2O is detected, an audible alarm is likewise output. Also, a light on the display panel of the base is lit to notify the user that N2O is being detected. The user could then take the appropriate action, by either shutting down the N2O source or using the necessary exhaust system to purge the N2O from the enclosed environment. The exhalent from the patient, once sampled by and passes through the measuring cell, is fed to a blower that vents the air out of the base housing.

The instant invention therefore defines an apparatus for detecting at least the presence of halogenated agents that comprises a base, a filter device removably coupled to the base, the filter device having an inlet for receiving exhaled air including halogenated agents from a patient or an anaesthesia machine and an outlet for outputting the filtered air. The base has an opening adapted to removably couple to the outlet of the filter device for receiving the filtered air. The base further houses a monitor system for detecting halogenated agents, if present, in the filtered air, and an alarm system for warning the presence of halogenated agents in the filtered air.

The present invention is also defined by an apparatus for filtering exhaled air having halogenated agents that comprises a filter container having an inlet for receiving the exhaled air. The filter container contains material adapted to adsorb a predetermined amount of halogenated agents and has an outlet for outputting air filtered thereby. The apparatus further includes a base having an opening for accepting the outlet of the filter container, the outlet and the opening cooperating to non-permanently secure the filter container to the base. The base further houses a monitor system fluidly connect to the opening for receiving the filtered air and adapted to detect halogenated agents in the filtered air, and an alarm system electrically connected to the monitor system for outputting an alarm signal when halogenated agents are detected in the filtered air. The alarm signal is removed when the filter container is replaced by a new filter container.

The present invention is further defined by a method of monitoring air exhalent by a patient that comprises the steps of connecting the patient to a breathing device, and connecting the output of the breathing device to an input of a filter device, the filter device having an outlet removably connected to the base, the base housing a monitor system and an alarm system. The method of the instant invention further utilizes the monitor system to sample and detect the presence of halogenated agents in the air filtered by the filter device, utilizes the alarm system to output an alarm if halogenated agents in the filtered air are detected by the monitor system, and replaces the filtered device when the output alarm is detected.

Another aspect of the instant invention is the detection of N2O from the exhaled air.

BRIEF DESCRIPTION OF THE FIGURES

The present invention will become apparent and the invention itself will be best understood with reference to the following description of the present invention taken in conjunction with the accompanying drawings, wherein.

DETAILED DESCRIPTION OF THE INVENTION

With reference to FIGS. 1–4, the halogenated agents and N2O detection device of the instant invention is shown to include a filter device in the form of a cannister 2 and a base or housing 4. Cannister 2 is configured in a conical shape, with an inlet port 5 and an outlet port 6. Stored in cannister 2 are activated charcoal or other materials that are adaptable for adsorbing halogenated agents or hydrocarbons that are part of the exhalent from a patient fed to the cannister via inlet 5. Some of the chemical materials that may be used are disclosed in the patents discussed in the Background of the Invention as for example those disclosed in the '980 patent, the disclosure relating to the chemical materials being incorporated by reference herein. To prevent the activated charcoals, in the event that charcoals are used, from falling out of cannister 2, respective sponge filters are provided at the inlet and outlet portions of the cannister. In regular use, the materials in cannister 2 are adapted to adsorb halogenated agents for approximately ten hours.

Figure 2:
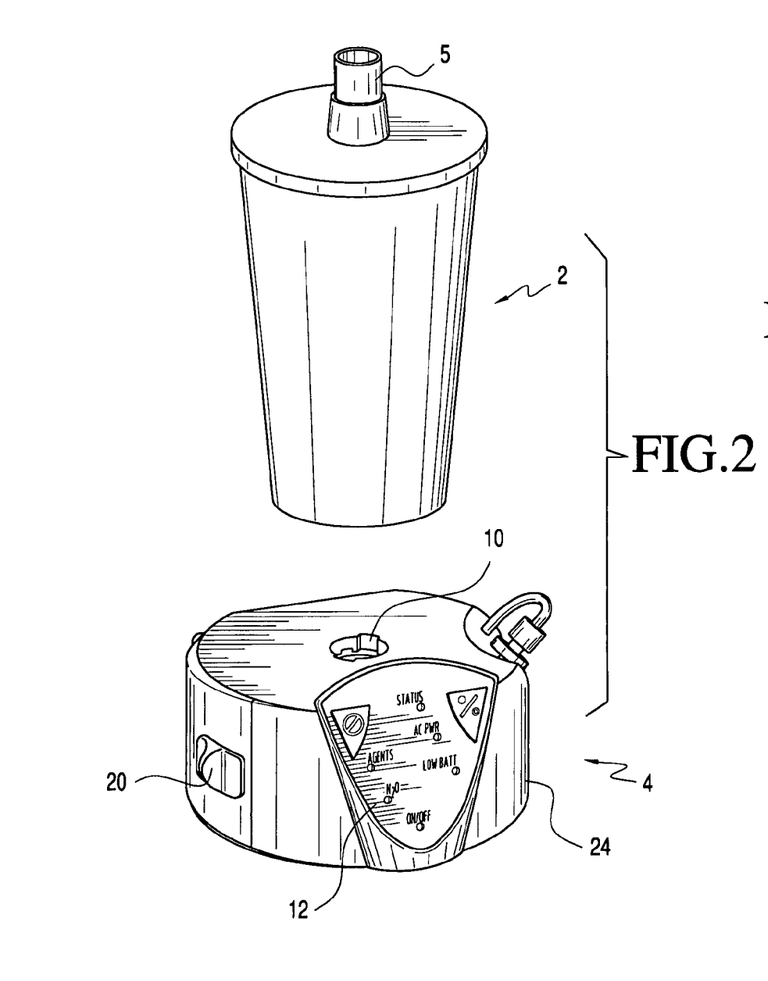
FIG. 2 is a perspective view showing the cannister portion being elevated from the base portion of the device of the instant invention.
Figure 3:
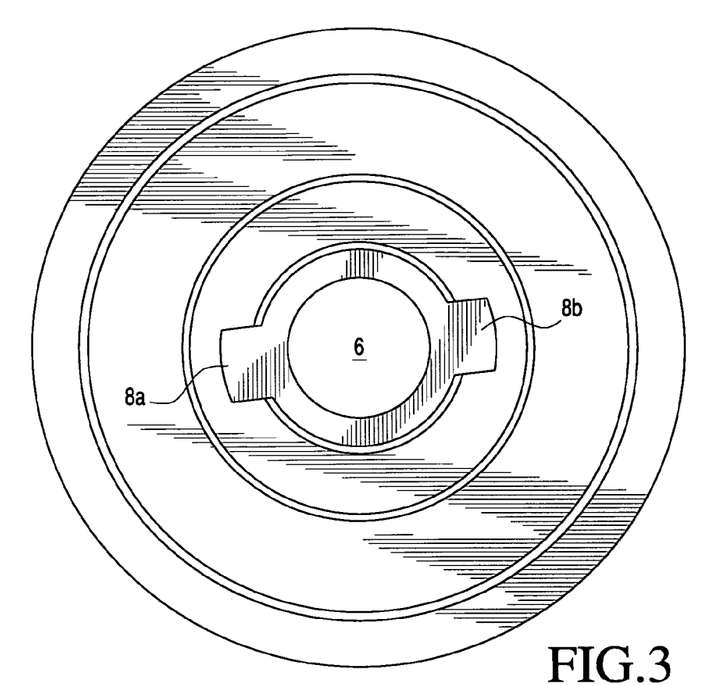
FIG. 3 is a plan view of the bottom of the cannister as shown in FIG. 2.
Figure 4:
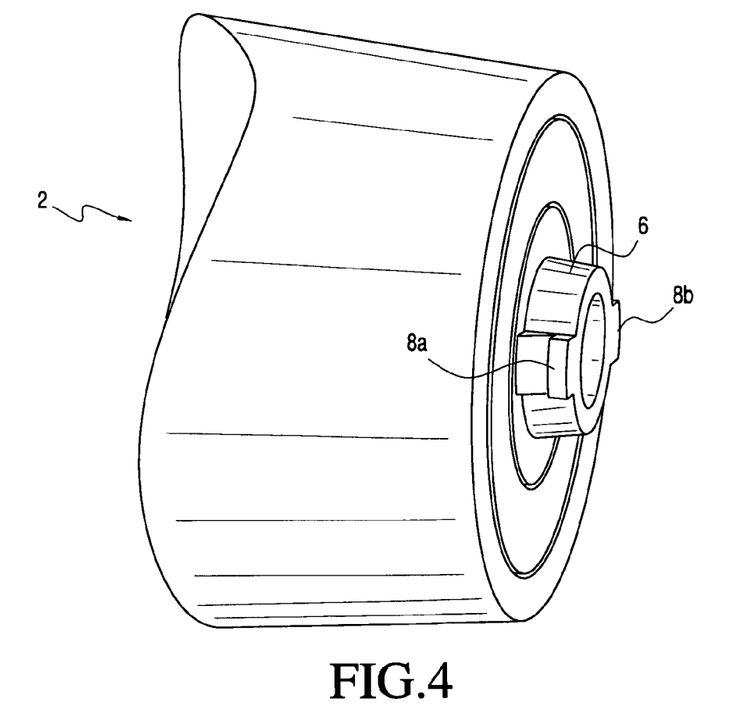
FIG. 4 is a perspective view of the bottom of the cannister of FIG. 2 showing in particular the mechanism used to couple the cannister to the base.

Outlet 6 of cannister 2 is configured to have two flanges 8a and 8b that allow a user to non-permanently secure or couple cannister 2 to base 4, with outlet 6 being mated to input port 10 of base 4. Flanges 8a and 8b act as a first half of a locking mechanism for securely coupling cannister 2 to a counterpart half of the locking mechanism at input port 10 of base 4, when cannister 2 is rotated. To remove cannister 2 from base 4, cannister 2 is rotated in a counter direction.

Figure 1:
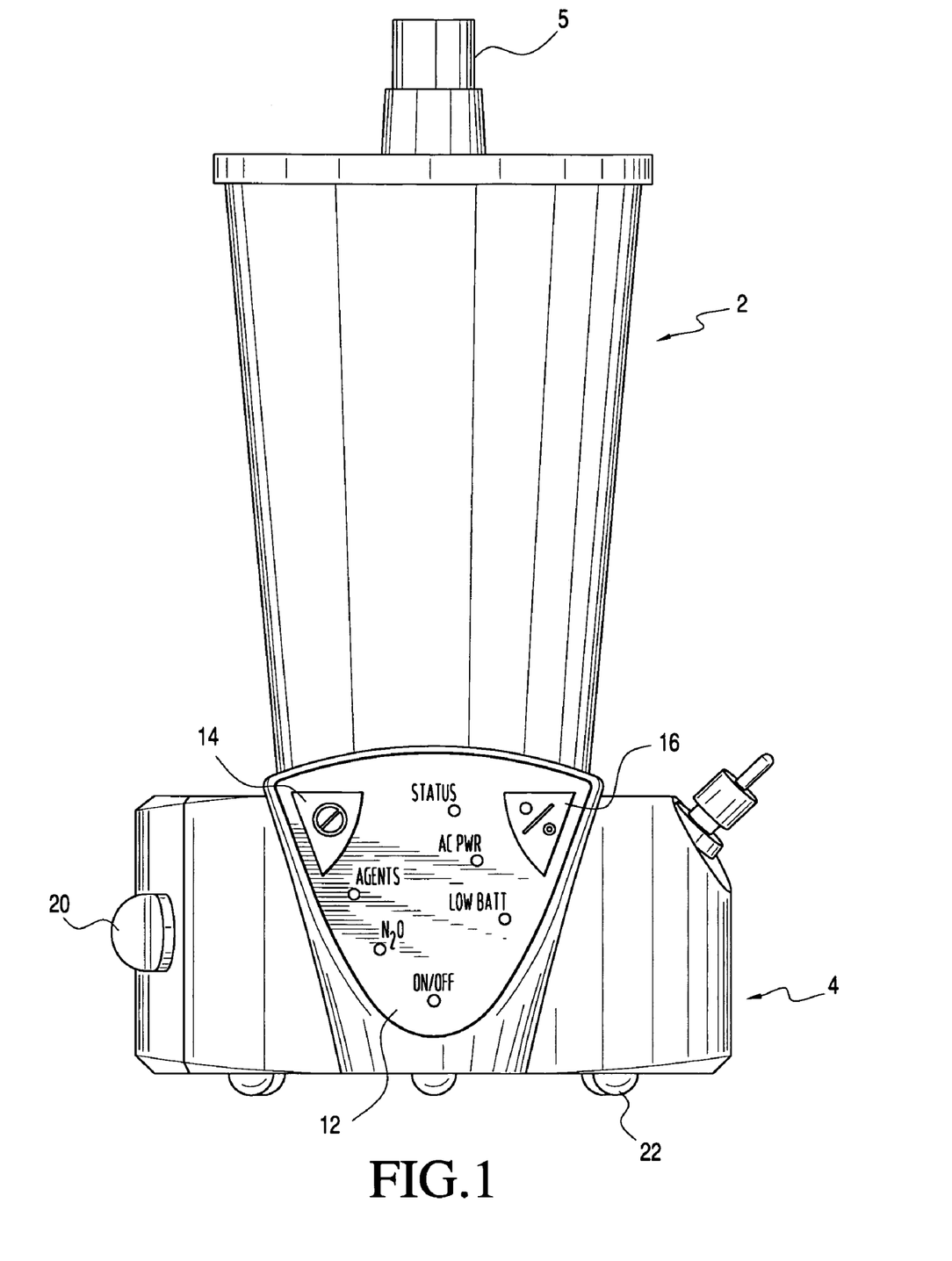
FIG. 1 is an assembled view of the device of the instant invention.

Base 4 has a display panel 12 that contains a number of indicator lights designating "STATUS", "AC PWR", "LOW BATT", "AGENTS", "$N_2O$" and "ON OFF". There are also two switches provided at the front panel. Switch 16 is the on/off switch while switch 14 is a button that, if pushed, would silence an audible alarm for a given period of time. A more detailed discussion of the various indicator lights will be given infra.

Figure 5:
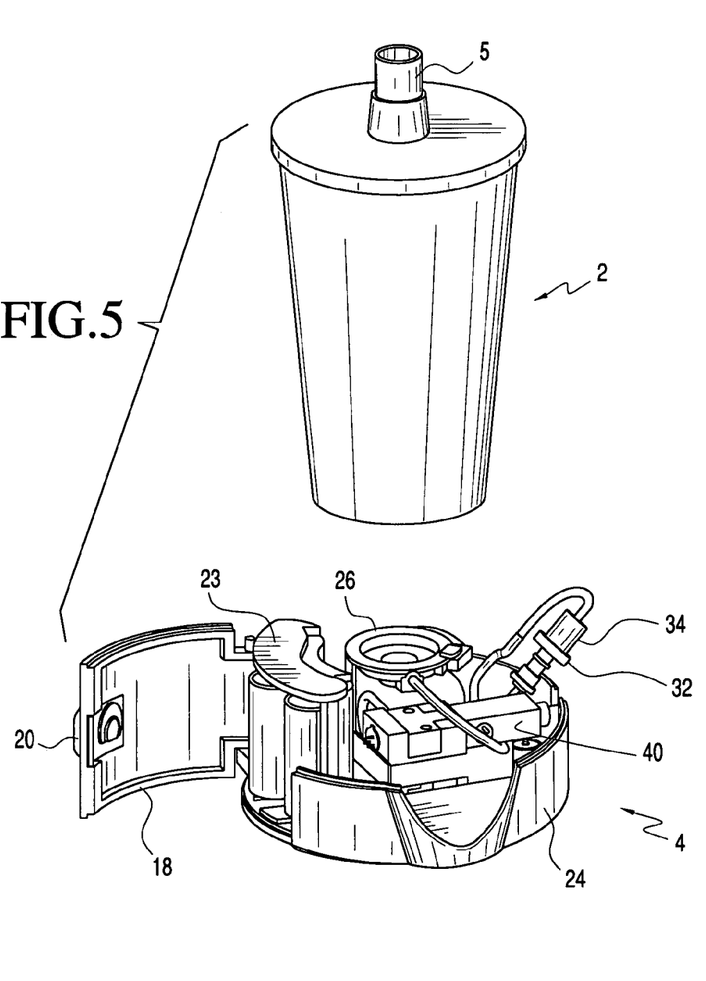
FIG. 5 is another view of the device of the instant invention with the cannister being separated from the base and the base semi-opened to show the various components housed therein.

Base 4 is accessible via a door 18, shown in FIG. 5. Door 18 is opened by the sliding of a knob 20. A number of footpads 22 are provided at the bottom of base 4 to lift the bottom surface of base 4 away from the top of any surface upon which base 4 rests.

FIG. 5 shows the various components and systems being housed in base 4. One of the components is battery 23, which, by opening door 18, could be accessed and replaced by the user. For the embodiment as shown, battery 23 is a set of 3 replaceable and non-rechargeable batteries having a total of approximately 4.5 volts.

Figure 6:
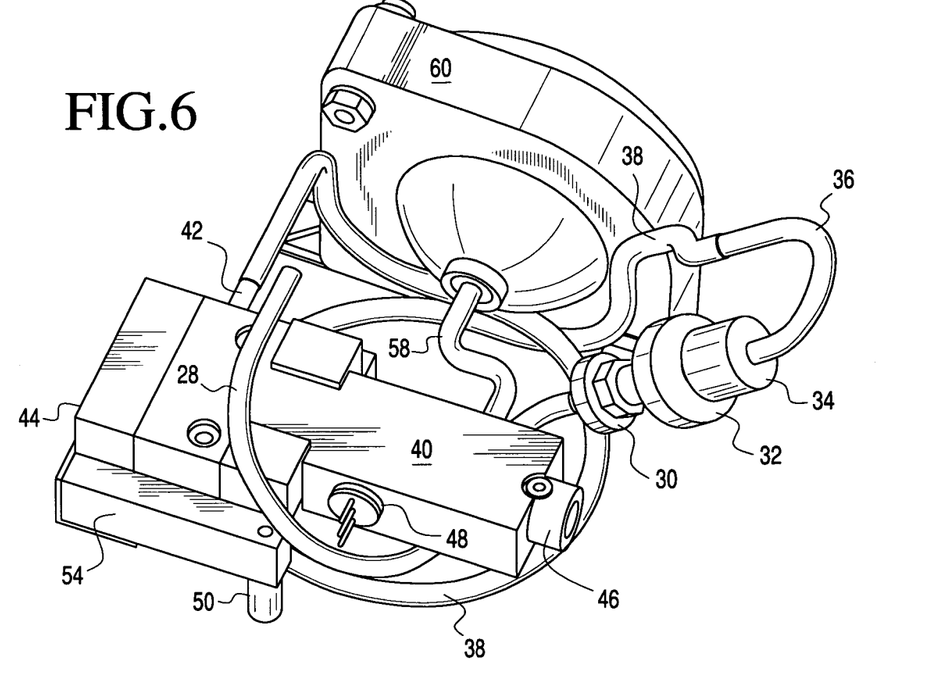
FIG. 6 is an exploded view of the various components housed in the base portion of the instant invention device.
Figure 7:
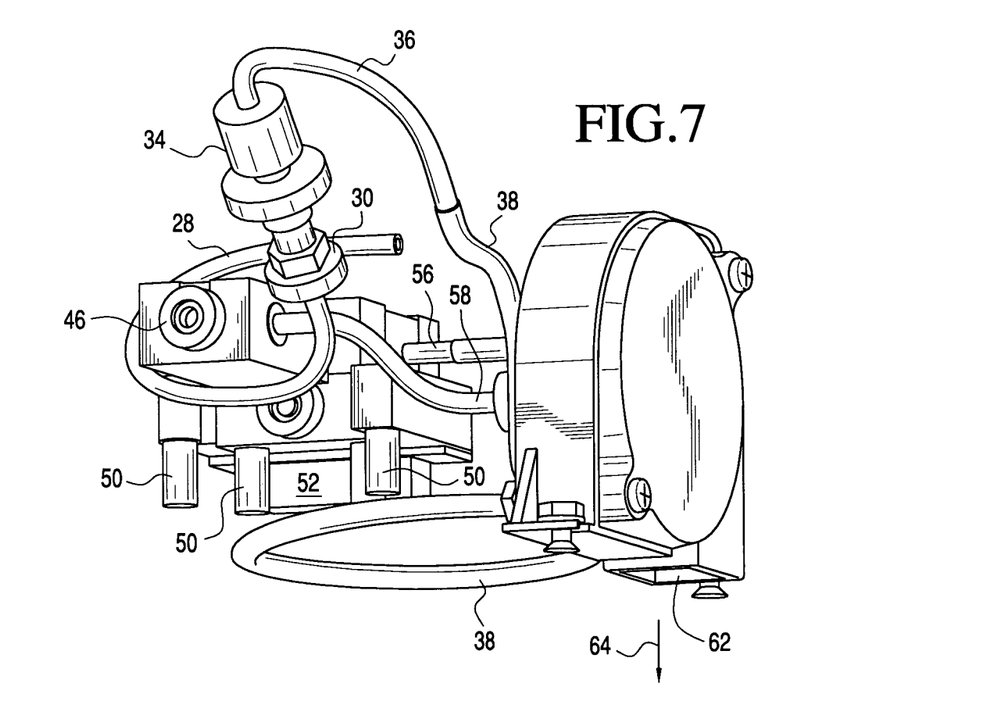
FIG. 7 is a different view of the various elements housed in the base of the instant invention.
Figure 8:
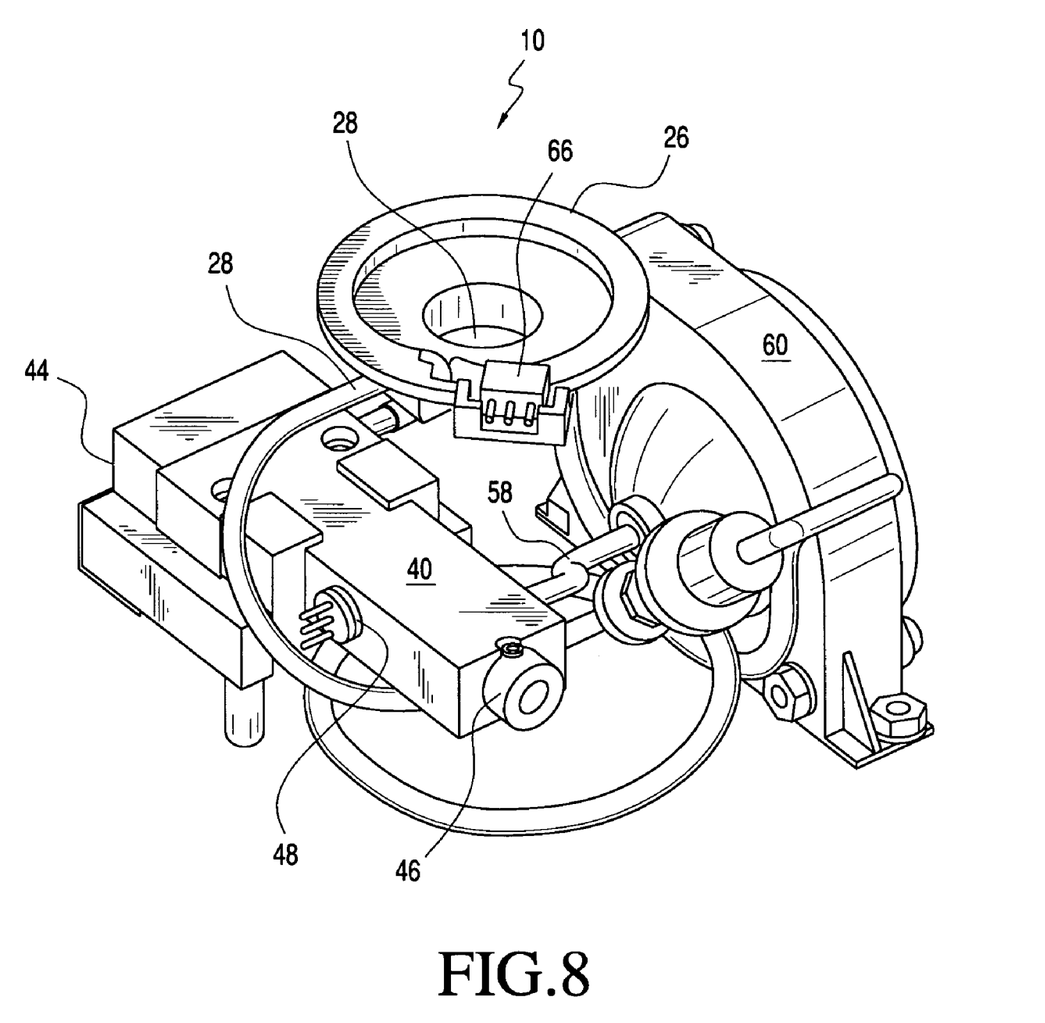
FIG. 8 is yet another exposed view of the various components housed in the base of the instant invention device.

For illustration simplicity, the various components housed in base 4 are shown to be freely standing without housing cover 24 in FIGS. 6, 7 and 8. FIG. 8 illustrates in more detail input port 10 at the base 4 which includes a cup-shape flange 26 that has an opening 28 for receiving the air filtered from cannister 2 and output from its outlet 6. Connected to the side of receiver port 26 at an opening (not shown) is a conduit or tube 28. With receiver port 26 removed from the illustrations of FIGS. 6 and 7, it can be seen that tube 28, which is a conventional plastics tubing that is adapted to carry the filtered air, has at its other end a bulkhead connector 30. A disposable contaminant filter 32 is removably coupled to connector 30 at its one end and a twist lock connector 34 at its other end. Contaminant filter 32 is used to filter out particles and dusts that may flow from cannister 2, due to the possible degradation of the sponge filters or the breakup of the activated charcoals inside cannister 2.

Connected to twist lock connector 34 is a clear plastics tube 36 that in turn is connected to a tube or conduit 38. Tube 38 is a tubing that is made of a moisture adsorbing material such as Nafion, which is a material similar to Gortex that allows moisture vapor to equilibrate. The purpose of tube 38 is to ensure that the humidity of the air being sucked into measuring cell 40 to which it is connected at its other end does not cause any condensation inside the cell. The length of tube 38 is designed to be of sufficient length to allow the moisture to equilibrate from the filtered air being routed or sucked into the measuring cell 40. Tube 38 is shown to have a loop configuration.

With its input 42 connected to tube 38, the filtered air is routed into measuring cell 40. In brief, cell 40 is configured to have the box-shaped dimension as shown, and includes a semiconductor sensor (FIG. 10) that changes its conductivity when the presence of halogenated agents is detected.

Also provided in measuring cell 40 is an optional N2O sensor that has an infrared (IR) measuring cell housed in cell portion 44, and a light source 46. The light from light source 46 passes through a filter wheel, so that the IR receiver can sequentially measure the signals in- and out-of the N2O absorption bands. If installed as an option, the gases from the patient would first pass the N2O sensor, before it is detected by the semiconductor sensor for halogenated agents.

The electrical connector to the semiconductor sensor is shown to be attached to a side of measuring cell 40, and is designated 48. A number of pins from connector 48 are used for connection to a circuit board (not shown) that is placed underneath the standoffs 50 for measuring cell 40, as best shown in FIG. 7. Also shown in FIG. 7 is a cover 52 that could be considered as part of measuring cell 40 and that is used to cover the spinning wheel of the N2O sensor. Additional cover plates 54 are provided on opposite sides of measuring cell 40. To these covers plates 54 the standoffs 50 are mounted.

The air and gas mixture sampled in measuring cell 40 is passed to an outlet 45 to which a tube 58 connects it to a blower 60. The fan in blower 60 creates a negative pressure to suck the filtered air from cannister 2 to base 4 for sampling and to vent the sampled air from base 4 through an exhaust port 62 as indicated by directional arrow 64.

A safety switch or sensor 66 is provided at input port 26 and proximate to the mouth of the port where the outlet of filter cannister 2 is accepted. The purpose of switch 66 is to detect whether cannister 2 is properly coupled to base 4. When cannister 2 is properly inserted to input portion 26, a flange at cannister 2 activates the switch. If switch 66 does not detect cannister 2, i.e., the filter for the halogenated agents is not attached, the system will not operate.

Figure 9:
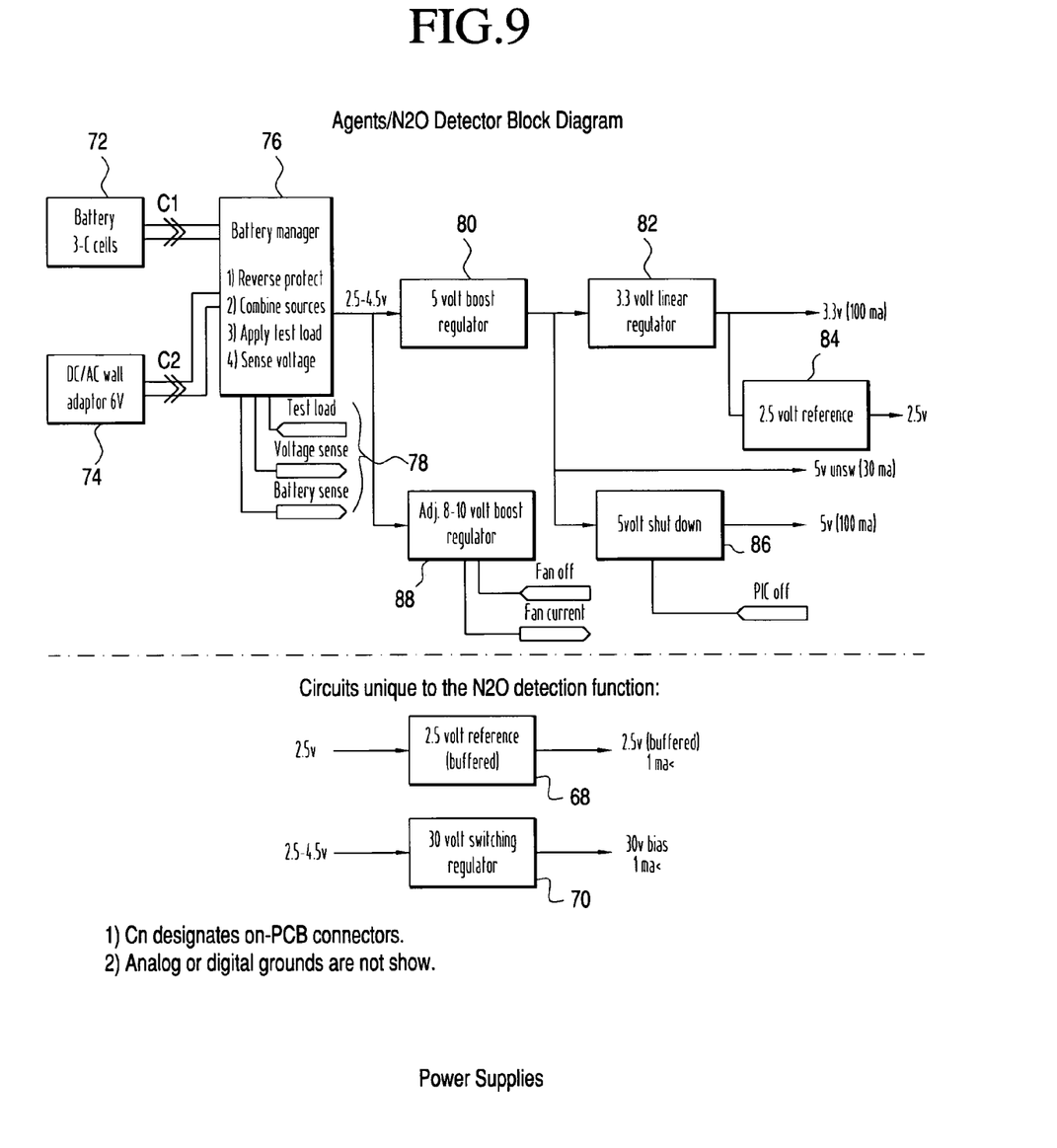
FIG. 9 is a block diagram illustrating the power supply circuits for providing power to operate the instant invention device.
Figure 10:
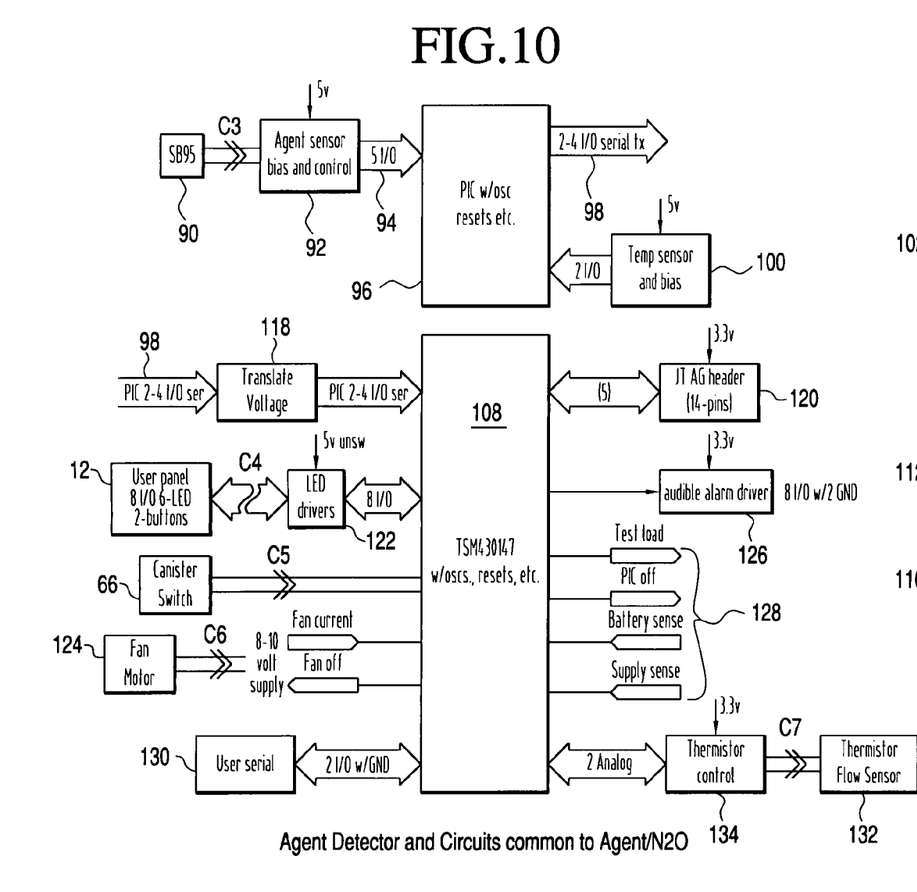
FIG. 10 is a block diagram illustrating the circuits for operating the halogenated agents sensor in the instant invention device.

FIG. 9 is a block diagram illustrating the power supplies used in the detection apparatus of the instant invention. With the disposable battery 23, the detection apparatus of the instant invention is usable in both the AC and DC modes. The circuits that are used to provide the voltages for the N2O sensor are designated 68 and 70 in FIG. 9. The 4.5 volt battery cell is referenced 72 in FIG. 9, with the wall adapter providing the AC power designated 74. The battery manager, designated 76, determines which voltage, either AC or DC, is to be used. The various inputs/outputs connected to battery manager 76, and designated 78, are used for diagnostic purposes. A 5 volt boost regulator, designated 80, receives the input voltage from battery manager 76, and provides the input voltage to a 3.3 volt linear regulator 82. The regulated 3.3 volt is stepped down to a 2.5 volt reference voltage. A 5 volt shutdown circuit 86 is used to turn the agent sensor on and off. To intermittently turn the N2O sensor on and off to preserve energy, the 3.3 volt linear regulator is relied upon. The controlling of the on and off of the shutdown circuit 86 is by way of a PIC processor, as shown in FIG. 10, which will be described in further detail later. A 8–10 volt boost regulator 88 controls the running of the exhaust fan. In sum, a number of output voltages are provided by the power supplies of the detection apparatus of the instant apparatus.

Figure 11:
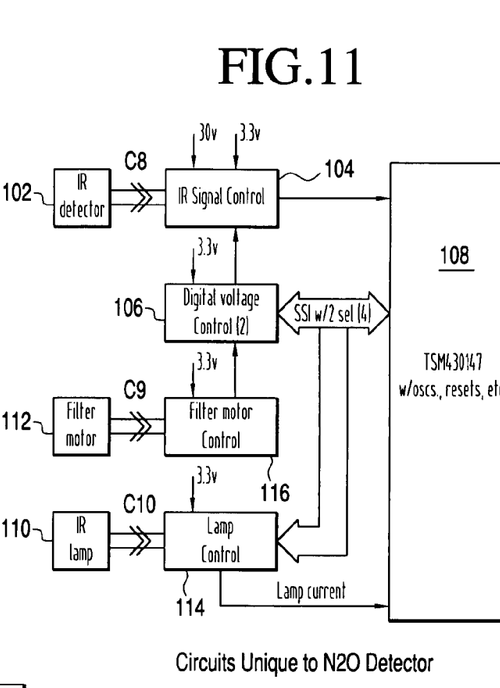
FIG. 11 is a block diagram illustrating the circuits unique to the N2O sensor of the instant invention.

FIGS. 10 and 11 illustrate the operation of the processors for controlling the sensing of the N2O sensor and the agents sensor. With reference to FIG. 10, note that a sensor, designated 90, is used for detecting the presence of halogenated agents. This sensor is a metal oxide semiconductor sensor manufactured under part number SB95 by the FiS Intelligent Sensors company and distributed by the Advanced Sensor Products company of Markham, Ontario. Sensor 90 outputs its signal to an agent sensor bias and control circuit 92, that conditions the signal and provides the same via an input 94 to a processor 96. Processor 96 is a PIC processor specially designed by the Microchip company with the appropriate algorithms for detecting the presence of halogenated agents and/or anesthetic gases from sampled gases. An output serial signal 98 is provided from processor 96 as an optional serial signal to communicate concentration numbers representative of the detected halogenated agents. These serial communication concentration numbers may be used in a display or other functions not associated with the detection apparatus of the instant invention. A temperature sensor and bias circuit 100 provides temperature sensing and biasing for processor 96. As noted earlier, the halogenated sensing system monitors the chemical changes of semiconductor sensor 90, in response to the sensing of presence of halogenated agents.

The circuits for the N2O detector are shown in FIG. 11. There, an IR detector 102, having part No. BXP-15 (M) manufactured by the Cal-Sensors Inc., of Santa Rosa, Calif., is connected to an IR signal control circuit 104. Also providing an input to signal control circuit 104 is a digital voltage control circuit 106 that is bidirectionally connected to a processor 108. Processor 108 may be a MSP430F147 or TMS430147 processor made by the Texas Instrument company. IR detector 102 detects the light output from an IR lamp 110, which output is filtered by a wheel, as represented by filter motor 112. Filter motor 112 controls the speed of the filter wheel to compensate for the wear of the wheel bearings. The control of the intensity of IR lamp 110 is via lamp control circuit 114, in reaction to signals from processor 108. The control of the filter motor, and the wheel driven thereby, is via filter motor control circuit 116.

In addition to providing control for the circuits of the N2O sensing system, processor 108 also controls various operations of the detection apparatus. As shown in FIG. 10, the serial output 98 from the agent sensor processor 96 is fed to a voltage translator 118 and input to processor 108. Also connected to processor 108 bidirectionally is JTAG header 120, which is a diagnostic port for a technician to test the functionality of processor 108. The display panel 12 shown in FIG. 1, is represented by the user panel circuit, and is shown to have six I/O LEDS and two button switches. The various LEDs and button switches are connected electrically to processor 108, with the LEDs being driven by an LED driver circuit 122. The cannister safety switch, designated 66 in FIG. 8, is also connected to processor 108 and controlled thereby. A fan motor 124, which is used to drive fan 60, is likewise controlled by processor 108. An audible alarm, driven by an audible alarm driver 126, is activated by processor 108, when either the presence of halogenated agents or N2O is detected, as noted above. A number of additional diagnostics contacts, designated 128, are provided to processor 108. An optional user serial circuit 130 may also be connected to processor 108 to provide the detection apparatus with the option of obtaining values from some other device. An optional thermistor flow sensor 132, and its control circuit 134, may also be connected to processor 108 to control the flow of air through the system for preventing occlusion of the system.

Figure 12:
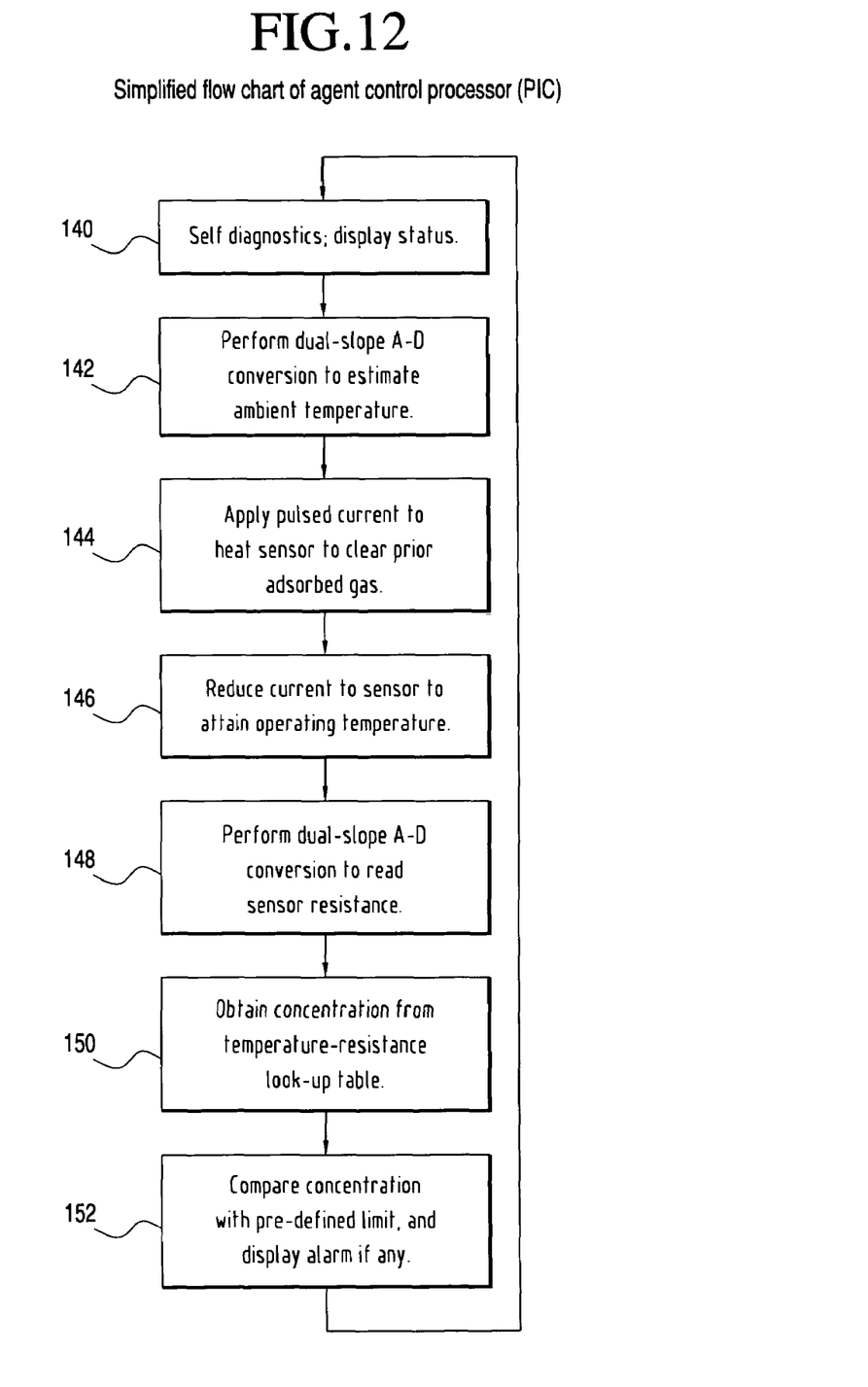
FIG. 12 is a flow diagram illustrating the operation of the processor that controls the sensor that senses the halogenated agents.

FIG. 12 is a simple flow chart illustrating the operation of PIC processor 96 that detects the presence of halogenated agents. The process begins with step 140 in which diagnostics are performed on the processor and the status of the processor is displayed. The ambient temperature is determined in step 142. Pulsed current is provided to heat the agent sensor and the prior adsorbed gas is purged, per step 144. The current is then reduced to attain the operating temperature for the sensor in step 146. The resistance of the semiconductor sensor is then determined in step 148. The concentration of halogenated agents, if any, detected by the sensor is obtained. The concentration of the halogenated agents is then compared with a predetermined threshold or limit. If the limit is exceeded, then it is assumed that halogenated agents are detected. At which time audible alarm driver 126 is activated. At the same time, the "AGENTS" LED on display panel 12 is lit to inform the user that halogenated agents have been detected, per step 152 of the process. To turn off the audible alarm for a predetermined period of time, as for example 3 minutes, a user can press button 14 located on the display panel 12. The operational process returns to step 140 if no halogenated agents are detected, so that the stream of air fed to measuring cell 40 is continuously monitored.

Figure 13:
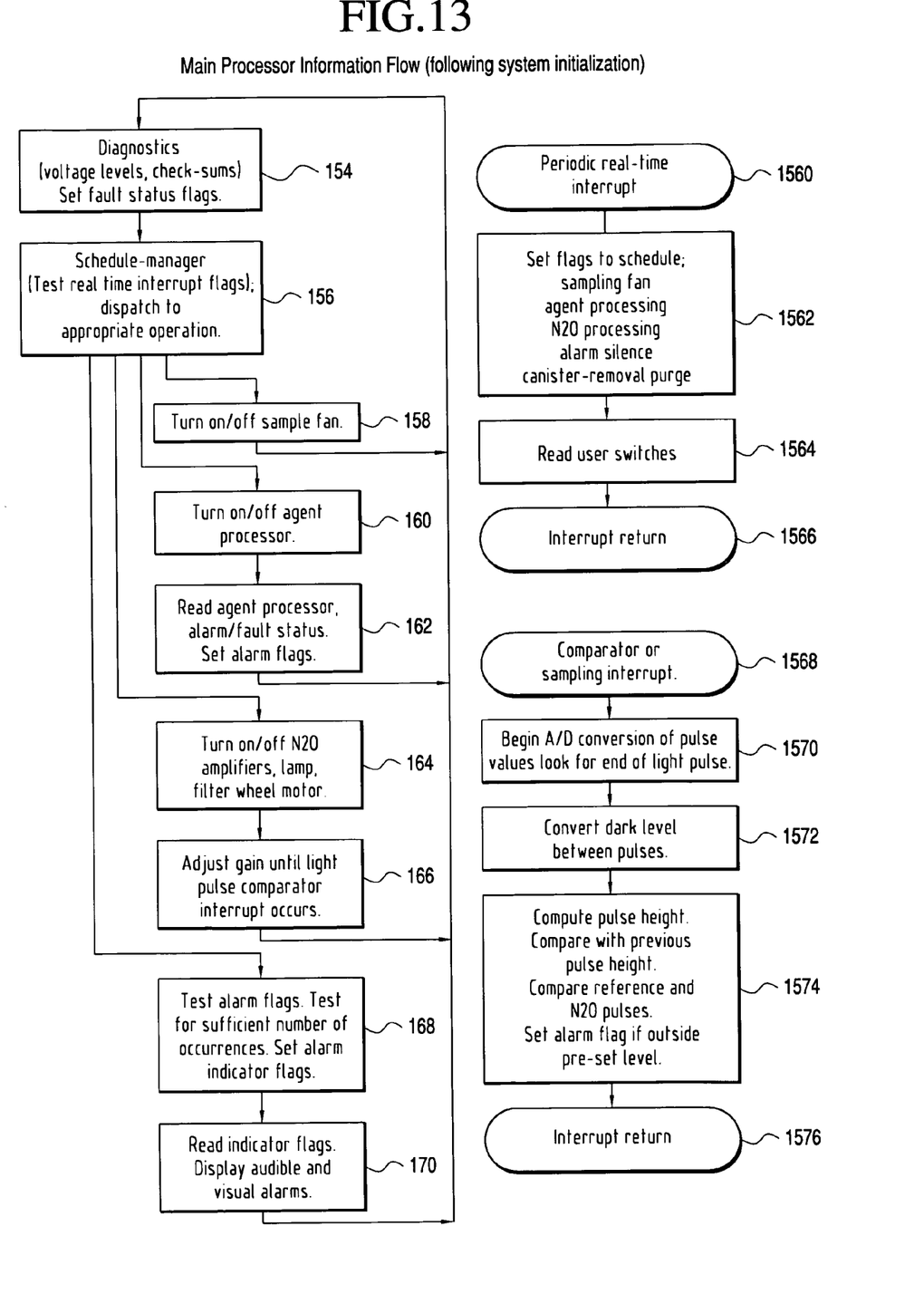
FIG. 13 is a flow chart illustrating the operation of the main processor of the instant invention device.

FIG. 13 shows the operational process of main processor 108. Starting with step 154, diagnostics are preformed by processor 108. Thereafter, per step 156, the various interrupts are tested and the appropriate operations started. The interrupts are shown by the side flow charts as the Period Real Time interrupt and the Comparator or Sampling interrupt.

For the periodic real time interrupt, designated 1560, the various flags are set and prepared per step 1562. The state of the switch operable by the user is read per step 1564. If there is an interrupt, the process returns to its periodic operation per step 1566. For the comparator or sampling interrupt 1568, the A/D conversion of the pulse values operation is performed in step 1570. The various levels of the pulses are converted per step 1572, and the determination of the presence of N2O is done per step 1574. And if the N2O concentration is determined to be greater than a preset level, the "N2O" LED is lit on display panel 12 and audible alarm 126 sounds. The interrupt then returns to await the next interrupt request per step 1576.

Returning to the operation of processor 108, the fan operation is controlled per step 158. Processor 96 is activated intermittently to control the sensing of the halogenated agents per step 160. The reading of the data from processor 96, the alarm/false status and the setting of the alarm flags are performed per step 162. Main processor 108 also controls the operation of the N2O sensor and its various components via steps 164 and 166. The setting of the test alarm flags and other miscellaneous operations are performed by steps 168 and 170, which operations are as shown in those blocks.

The invention claimed is:

1. Apparatus for detecting at least presence of halogenated agents, comprising: a base, a filter device including halogenated agent absorbent material removably coupled to said base, said filter device having an inlet for receiving exhaled air including halogenated agents from a patient or an anaesthesia machine and an outlet for outputting the filtered air, said base having an opening adaptable to removably couple to the outlet of said filter device for receiving the filtered air, said base housing a monitor system for detecting halogenated agents, if present, in the filtered air, and an alarm system for warning the presence of halogenated agents in the filtered air.

2. Apparatus of claim 1, wherein said monitor system is further adaptable for detecting the presence of N2O (Nitrous Oxide) from the exhaled air.

3. Apparatus of claim 1, wherein said filter device comprises a cannister and wherein the outlet is removably matable with said opening of said base to securely mount said cannister to said base, wherein the halogenated agent absorbent material is stored in said cannister for absorbing the halogenated agents from the exhaled air.

4. Apparatus of claim 3, further comprising a safety switch located proximate to said opening at said base for detecting whether the outlet of said cannister is securely mated to said opening of said base.

5. Apparatus of claim 1, further comprising a display panel having thereon at least one indicator responsive to said alarm system for indicating the presence of N2O, and another indicator for providing an alarm that halogenated agents are no longer being absorbed by said filter device.

6. Apparatus of claim 1, wherein said base further houses a first conduit extending from said opening to one end of a contaminant filter, said contaminant filter being replaceable and has its other end connected to a second conduit that routes the filtered air to said monitor system for detecting the presence of the halogenated agents and N2O.

7. Apparatus of claim 6, wherein the filtered air sampled by said monitor system is thereafter routed by a third conduit to an air blower housed in said base, said blower venting the filtered air from said base to the environment.

8. A method of monitoring air exhaled by a patient, comprising the steps of:
connecting the patient to a breathing device;
connecting the output from the breathing device to an input of a filter device, said filter device having an outlet removably connected to a base, said base housing a monitor system and an alarm system;
utilizing said monitor system to sample and detect the presence of halogenated agents in the air filtered by said filter device;
utilizing said alarm system to output an alarm if halogenated agents in the filtered air are detected by said monitor system; and
replacing said filter device when said output alarm is detected.

9. Method of claim 8, further comprising the steps of:
utilizing said monitor system to detect the presence of N2O (Nitrous Oxide) in the filtered air; and
outputting a N2O alarm if N2O is detected.

10. Method of claim 8, further comprising the step of:
venting the filtered air from said base.

11. Method of claim 8, further comprising the steps of:
providing a switch proximate to an opening at said base whereto the outlet of said filter device is removably coupled, said switch detecting the coupling of said filter device to said base; and
outputting an other alarm if said switch does not detect said filter device being coupled to said base.

12. Method of claim 8, further comprising the steps of:
providing at said base a display panel having thereon at least one indicator responsive to said alarm system for indicating the presence of N2O, and another indicator for providing an alarm that halogenated agents are no longer being absorbed by said filter device.

13. Apparatus for filtering exhaled air having halogenated agents, comprising:
a filter container having an inlet for receiving the exhaled air, said filter container containing material adapted to absorb a predetermined amount of halogenated agents, said filter container having an outlet for outputting air filtered thereby; and a base having an opening for accepting said outlet of said filter container, said outlet and said opening cooperating to non-permanently secure said filter container to said base, said base housing a monitor system fluidly connected to said opening for receiving the filtered air and adapted to detect halogenated agents in the filtered air, said base further housing an alarm system electrically connected to said monitor system for working cooperatively with said monitor system to output an alarm signal when halogenated agents are detected by said monitor system in the filtered air; wherein said alarm signal is removed when said filter container is replaced by a new filter container.

14. Apparatus of claim 13, wherein said monitor system is further adapted to detect the presence of N2O (Nitrous Oxide), and wherein said alarm system outputs a N2O alarm when N2O is detected by said monitor system in the filtered air.

15. Apparatus of claim 13, wherein said filter container comprises a conical shaped cannister that has at the outlet a first connecting portion for non-permanently mating with a counterpart connecting portion at said opening of said base to secure said cannister to said base.

16. Apparatus of claim 13, further comprising a safety switch located proximate to said opening at said base for detecting whether said filter container is secured to said base.

17. Apparatus of claim 13, wherein said base further comprises a display panel having thereon at least one indicator responsive to said alarm system for indicating the presence of N2O, and another indicator for providing an alarm that halogenated agents are no longer being absorbed and said filter container needs to be replaced.

18. Apparatus of claim 13, further comprising an air blower housed in said base for accepting the filtered air from said monitor system, said blower purging the filtered air from said base to the environment.

* * * * *